(12) United States Patent
Okinishi

(10) Patent No.: US 7,347,550 B2
(45) Date of Patent: Mar. 25, 2008

(54) OPHTHALMOLOGIC IMAGE TAKING APPARATUS

(75) Inventor: Satoru Okinishi, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 549 days.

(21) Appl. No.: 10/916,266

(22) Filed: Aug. 11, 2004

(65) Prior Publication Data

US 2005/0036111 A1     Feb. 17, 2005

(30) Foreign Application Priority Data

Aug. 13, 2003     (JP) .............................. 2003-207471

(51) Int. Cl.
*A61B 3/14* (2006.01)
*A61B 3/10* (2006.01)

(52) U.S. Cl. ...................... 351/206; 351/221

(58) Field of Classification Search ........ 351/200–208, 351/211, 214, 221–223, 237, 243
See application file for complete search history.

(56) References Cited

U.S. PATENT DOCUMENTS

| 5,341,180 | A | * | 8/1994 | Isogai et al. ............. 351/206 |
| 5,557,321 | A | * | 9/1996 | Kohayakawa et al. ..... 348/78 |
| 5,844,659 | A | * | 12/1998 | Isogai ..................... 351/208 |
| 6,022,108 | A | * | 2/2000 | Yoshida et al. .......... 351/208 |
| 6,179,421 | B1 | | 1/2001 | Pang ....................... 351/205 |
| 2002/0021411 | A1 | | 2/2002 | Wilson .................... 351/222 |
| 2002/0131017 | A1 | | 9/2002 | Kishida et al. ........... 351/206 |

FOREIGN PATENT DOCUMENTS

| JP | H5-137696 | 6/1993 |
| JP | H6-165763 | 6/1994 |
| JP | H9-173295 | 7/1997 |
| JP | 11-070080 | 3/1999 |
| WO | 2004/045401 | 6/2004 |

OTHER PUBLICATIONS

Korean Office Action mailed Feb. 28, 2006 with English Translation (relevant portion only).

* cited by examiner

*Primary Examiner*—M. Hasan
(74) *Attorney, Agent, or Firm*—Morgan & Finnegan L.L.P.

(57) ABSTRACT

Disclosed is an ophthalmologic image taking apparatus in which, when a processed medical image is read, an intended purpose of image taking can be intuitively and speedy understood, so that an image reading operation is accurately and efficiently conducted. The ophthalmologic image taking apparatus includes: an image taking optical system for taking an optical image of an eye to be examined; an electronic image taking portion for converting the optical image of the eye to be examined, which is formed by the image taking optical system, into digital image data; an input portion for inputting at least a magnification; a processing portion for processing the digital image data at the magnification at least for a magnification changing process; a display portion for displaying an image obtained by the magnification changing process; and an image storing portion for storing the digital image data and at least the magnification. Further, a control unit controls the image storing portion to store the digital image data and at least the magnification in association with each other.

3 Claims, 17 Drawing Sheets

OPHTHALMOLOGIC IMAGE TAKING APPARATUS

BACKGROUND OF THE INVENTION

1. Field of the Invention

The present invention relates to image taking using an ophthalmologic image taking apparatus, and more particularly to a technique suitable for displaying an image in the ophthalmologic image taking apparatus.

2. Related Background Art

It is naturally required for a medical image such as an ophthalmologic image to be accurately recorded as an image. In addition, an equally important requirement in the recording of the medical image such as the ophthalmologic image is to record information on an intended purpose of image taking for an image to be taken, that is, why the image needs to be taken.

The intended purpose of image taking (hereinafter referred to as "image taking purpose") of the medical image can be recorded by leaving a record of image taking on a patient chart, an image taking instruction sheet, or the like, writing the record into the taken image, or adding data of the record to the taken image in the case of, for example, an electronic image.

Note that it is inefficient to refer to such record in an actual image diagnosis every time the necessity arises. Therefore, it is preferable to conduct the diagnosis while intuitively reading the image taking purpose from the image. Thus, for example, a site of interest is taken so as to be located at the center of a screen, or image taking is conducted with the site magnified. An image reader who views an image taken by such an image taking method can intuitively understand the image taking purpose of the image in a short time, so that image reading and diagnosis can be efficiently performed. Such a method is disclosed in, for example, Japanese Patent Application Laid-Open No. H05-137696, Japanese Patent Application Laid-Open No. H06-165763, or Japanese Patent Application Laid-Open No. H09-173295.

However, according to a photography process using a silver salt material, which has been widely conducted up to now, when a magnified image is to be taken as described above, it is necessary to optically magnify the image and the taken image exists only as the magnified image. Even in a digital photography process which is widely used in recent years, of course, it is possible to conduct the magnified image taking while examining an image taking site at increased magnifications during image taking.

In this example, the image to be examined is viewed in a state in which the image is magnified with the image taking site as the center thereof. Therefore, the image reader can intuitively understand the image taking purpose as described above. However, the image reader cannot view a site other than the region of the image, with the result that it is necessary to find an image including a required site from other images.

On the other hand, because an electronic image is easy to handle, the following operation is possible. That is, an image is taken at a wide view angle, that is, at low power. When detailed examination is required, the image is magnified as needed using, for example, a viewer function of a personal computer by the image reader. Therefore, it is possible to reduce the number of separate image takings with respect to the magnified image and the wide angle image.

In this example, a wide range image can be viewed, so that the degree of freedom of selection with respect to the magnifying power of the image and the magnified site is high. However, to view the magnified image, it is necessary to conduct predetermined operations such as magnifying of the image and selection of a magnifying region, so that image viewing is complicated. In addition, it is extremely hard to understand the image taking purpose of the image, such as the site of interest and the image taking power (that is, the degree of attention to the site) for the image taking, from the image alone.

In an example of an eye fundus image, there are cases where a wide view angle image mainly focused on a posterior fundus including a papilla and a macula is taken in addition to an image of a lesion present in an eye fundus peripheral portion in order to obtain as much information as possible from a single photograph for reducing a burden on a patient. In addition, there are cases where it is difficult to take an image mainly focused on the lesion present in the eye fundus peripheral portion because of poor mydriasis or a defect of the eye to be examined, such as a cataract. When an image in which the lesion portion is shown at some location is just taken, it is hard to intuitively understand an image taking purpose from the single image alone. That is, it is difficult to intuitively understand that the subject of the greatest interest here is the lesion portion present in the peripheral portion although the posterior fundus is shown in the center of the image, or that the lesion portion is present at some position on the image.

When the image taking is conducted while viewing an examination image that has been subjected to an image process such as edge enhancement, contrast enhancement, RGB-corrected display, or band compression and extension according to a subject to be examined, it is possible to more clearly examine a subject image to be taken. Therefore, when such an image is taken and left, this can greatly contribute to intuitively understanding the image taking purpose upon image reading. However, an original image which has not been subjected to the image process cannot be viewed. Thus, a serious problem involves from the viewpoint of a medical image if the original image cannot be viewed and only the intentionally processed image can be viewed.

SUMMARY OF THE INVENTION

The present invention has been made in view of the above-mentioned problems. An object of the present invention is to provide an ophthalmologic image taking apparatus capable of displaying an image in a favorably manner.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENTS

Figure 1:
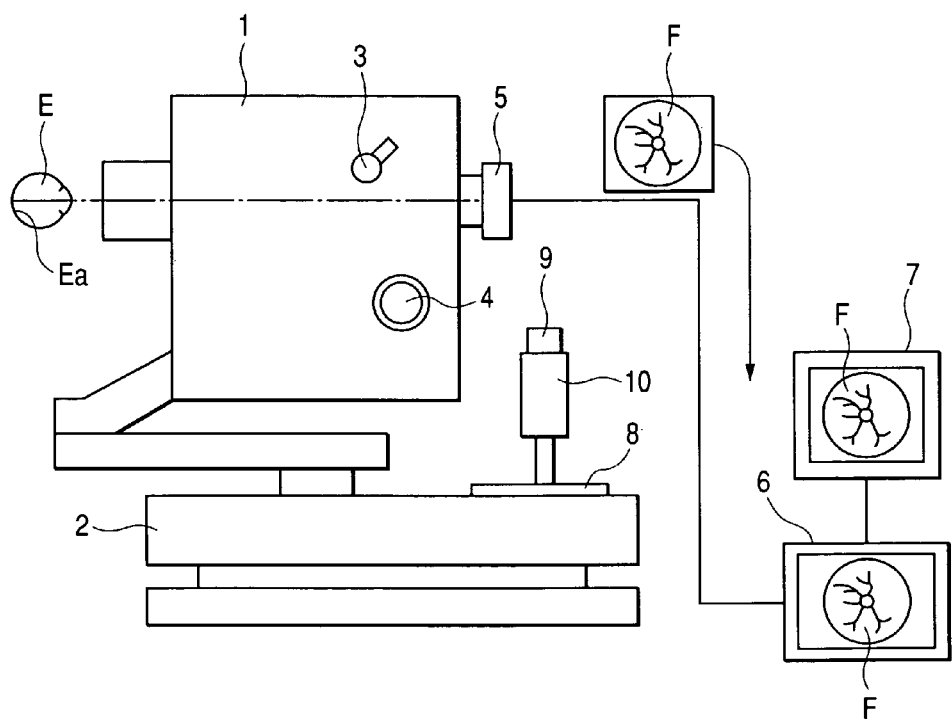
FIG. 1 is a schematic external view showing an apparatus to the present invention.

Preferred embodiments of the present invention will now be described in detail in accordance with the accompanying drawings.

The present invention will be described in detail with reference to embodiments shown in the drawings.

FIG. 1 is a schematic external view showing an apparatus according to the First Embodiment of the present invention. A case 1 including an optical system is mounted on a stage 2 so as to be three-dimensionally movable in its position and posture for alignment with an eye to be examined E. A magnification changing switch 3, a focus knob 4, and an electronic image taking means 5 composed of a digital camera or the like are mounted on the case 1. An output of the electronic image taking means 5 is connected with a display means 7 through an image handling means 6. An operating panel 8 having plural kinds of switches is provided on the stage 2. A joystick 10 having an image taking switch 9 at a top thereof is provided on the operating panel 8.

Figure 2:
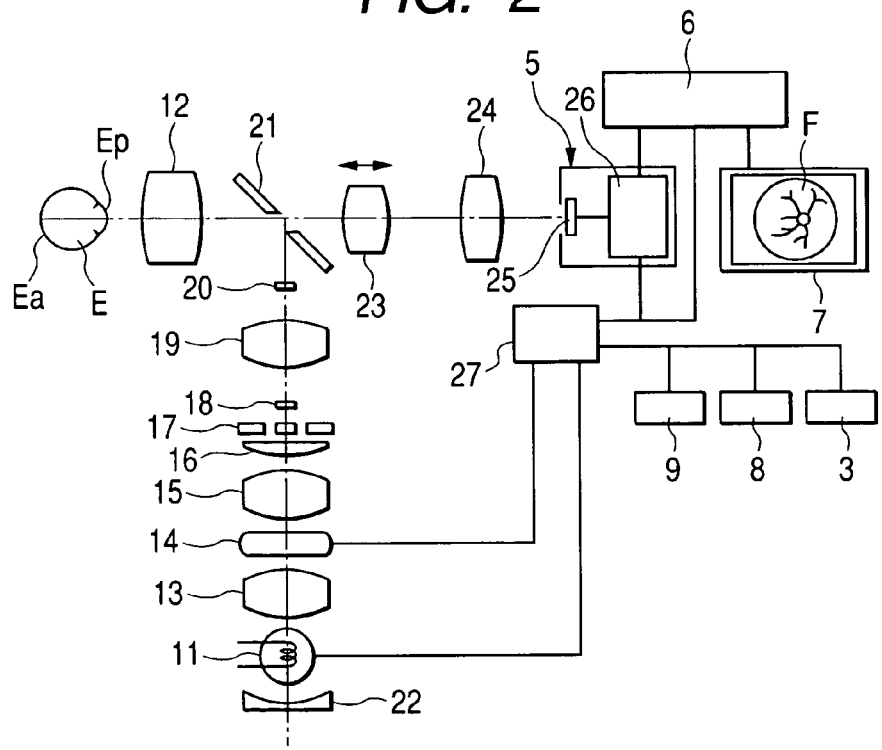
FIG. 2 is a diagram showing optical and electrical structures of the apparatus.

FIG. 2 is an optical and electrical structural diagram showing an inner portion of the case 1 applied to an eye fundus camera. A condenser lens 13, a strobe tube 14 serving as an image taking light source, a condenser lens 15, a field lens 16, a ring slit 17, a light shielding member 18 for blocking harmful light, a relay lens 19, a light shielding member 20, and a holed mirror 21 are disposed from an examination light source 11 side on an optical path from the examination light source 11 serving as a continuous light emitting source to an objective lens 12. A concave mirror 22 is disposed in the rear of the examination light source 11.

A focus lens 23 which is movable in the optical axis direction by the focus knob 4, an imaging lens 24, and an electronic image taking means 5 are disposed in the rear of the holed mirror 21. The electronic image taking means 5 includes an image taking element 25 and an image taking circuit 26. The image taking element 25 converts into a charge an optical image of an eye fundus portion Ea which is formed at "image taking optical system basic imaging power" which is minimal imaging power (widest view angle) of an image taking optical system. The image taking circuit 26 reads as a signal waveform the charge from the image taking element 25 while effecting synchronous control.

An output of the image taking circuit 26 is connected with the image handling means 6 and a control means 27. The image handling means 6 is connected with the display means 7 and the control means 27. The control means 27 is connected with the examination light source 11, the strobe tube 14, the magnification changing switch 3, the operating panel 8, and the image taking switch 9.

The control means 27 receives operation signals from the magnification changing switch 3 and the image taking switch 9 and controls the entire apparatus including the examination light source 11 and the strobe tube 14 according to the operation signals. In addition, the control means 27 communicates control signals, trigger signals, input data, and the like to and from the electronic image taking means 5 and the image handling means 6.

Figure 3:
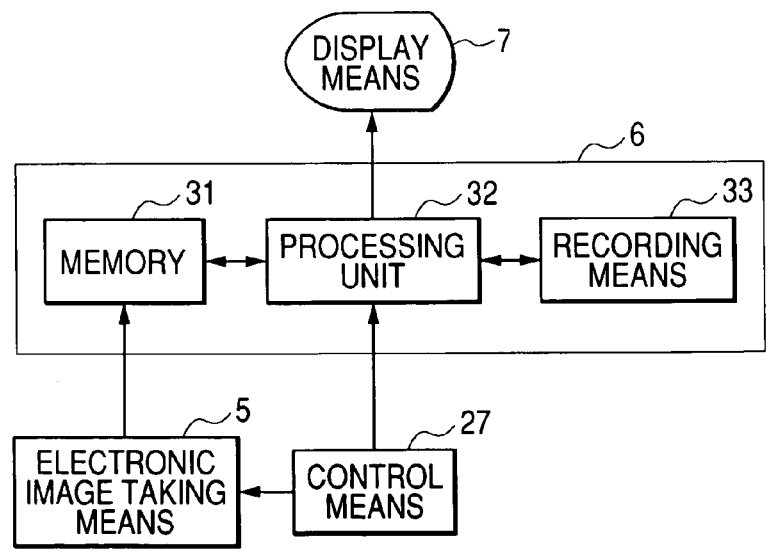
FIG. 3 is a block diagram showing an image handling means.

FIG. 3 is a block diagram showing the image handling means 6. The image handling means 6 includes a memory 31, a processing unit 32, and a recording means 33. The processing unit 32 is connected with the memory 31 and the recording means 33. The memory 31 is connected with an output of the electronic image taking means 5. The processing unit 32 is connected with the control means 27 and the display means 7.

Illumination light emitted from the examination light source 11 or the strobe tube 14 is formed into a ring shape by the field lens 16 and the ring slit 17 through the condenser lenses 13 and 15. The illumination light transmits through the relay lens 19 and the light shielding members 18 and 20, which constitute an illumination optical system. Then, the illumination light is reflected on a peripheral portion of the holed mirror 21 to be irradiated on the eye fundus portion Ea of the eye to be examined E through the objective lens 12.

Reflection light from the eye fundus portion Ea transmits through the objective lens 12, a hole portion of the holed mirror 21, the focus lens 23, and the imaging lens 24, and an image of the reflection light is taken by the electronic image taking means 5. The objective lens 12, the holed mirror 21, the focus lens 23, the imaging lens 24, the electronic image taking means 5 constitute the image taking optical system.

The signal waveform read from the image taking element 25 of the electronic image taking means 5 is AD-converted into digital image data by the image taking circuit 26. The digital image data is output together with a synchronous signal to the image handling means 6. The image data and the synchronous signal which are input to the image handling means 6 are temporarily stored in the memory 31. The processing unit 32 performs a predetermined process on the image data stored in the memory 31 and causes the recording means 33 to store the processed image data or the display means 7 to display an image. As described later, the processing unit 32 changes data processing contents according to an input from the control means 27.

When an image of the eye fundus portion Ea is to be taken, in order to perform an alignment with an image taking site and focusing thereon, the apparatus is generally operated in a moving image mode. When operating in the moving image mode, the control means 27 instructs the image handling means 6 and the electronic image taking means 5 to operate in the moving image mode. In response to this, the electronic image taking means 5 successively takes image data of the eye fundus portion Ea corresponding to several frames per second to several tens of frames per second. The image handling means 6 acquires the taken image data. An image is successively prepared for each frame based on the plural image data acquired by the image handling means 6. The prepared images are continuously displayed on the display means 7 in real time to provide a moving image of the eye to be examined E to an examiner.

The examiner conducts an alignment with a predetermined site of the eye fundus portion Ea and focusing thereon while examining the moving image of the eye to be examined E which is displayed on the display means 7. Then, when the image taking switch 9 provided on the joystick 10 is pressed, the control means 27 performs the following operation based on a known control method. That is, a predetermined amount of light is emitted from the strobe tube 14 for a predetermined time. Simultaneously, the control signals and the trigger signals are sent to the electronic image taking means 5 and the image handling means 6 to stop the acquisition of the moving image. A still image (one frame image) of the eye fundus portion Ea is taken by the electronic image taking means 5 in synchronization with the light emission of the strobe tube 14. A taken still image F shown in FIGS. 1 and 2 is stored in the image handling means 6. Simultaneously, the still image F is displayed on the display means 7.

Figure 4:
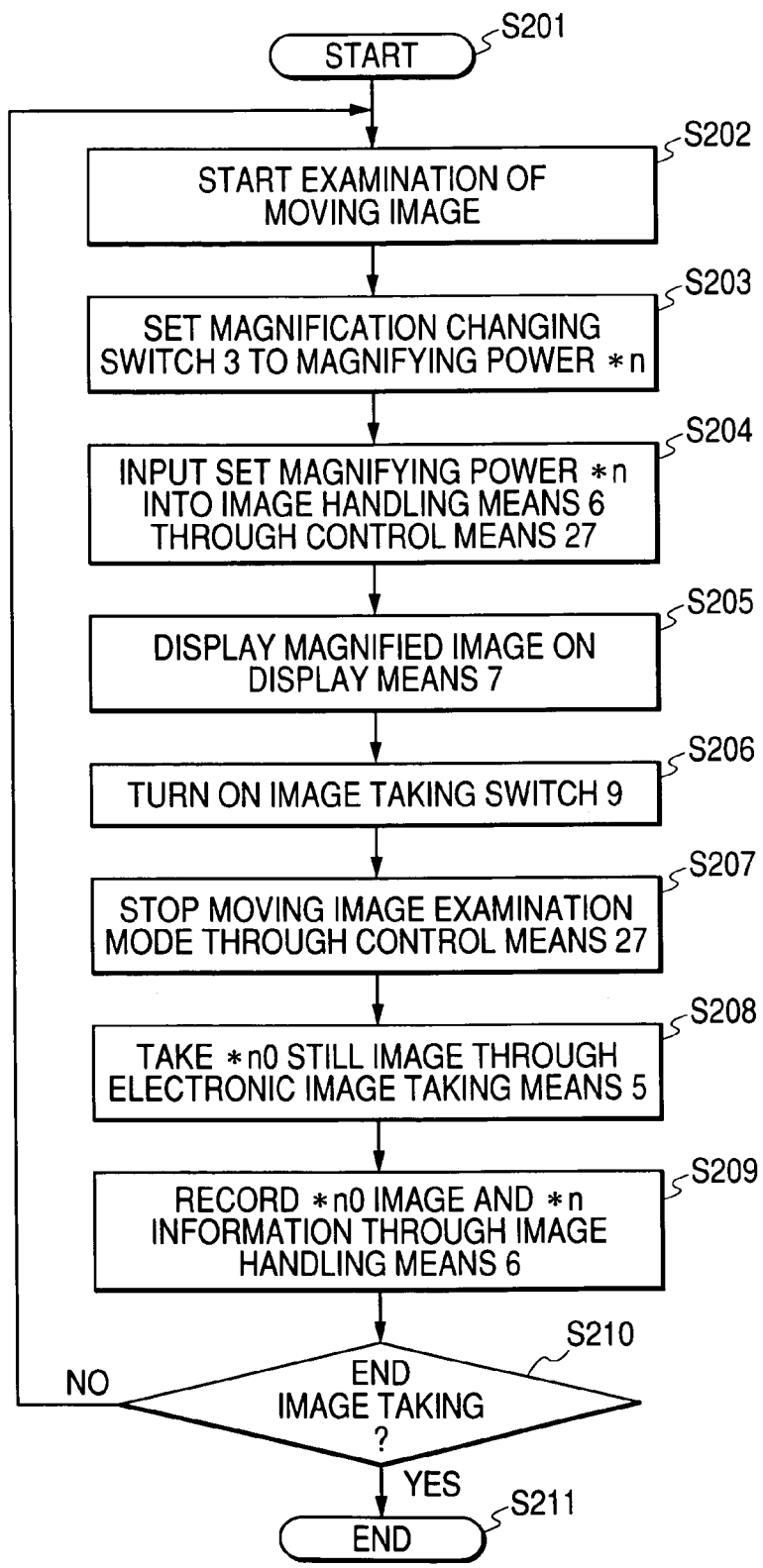
FIG. 4 is a flow chart showing an image taking operation involving magnification changing.

FIG. 4 is a flow chart in the case of magnified image taking. In the magnified image taking, as shown by an arrow in FIG. 5, the magnification changing switch 3 is operated as indicated by an arrow in FIG. 5 during the above-mentioned moving image examination to set magnifying power to n-times (*n) (steps S201 to S203). The magnifying power *n input from the magnification changing switch 3 is input to the image handling means 6 through the control means 27 (step S204).

Figure 5:
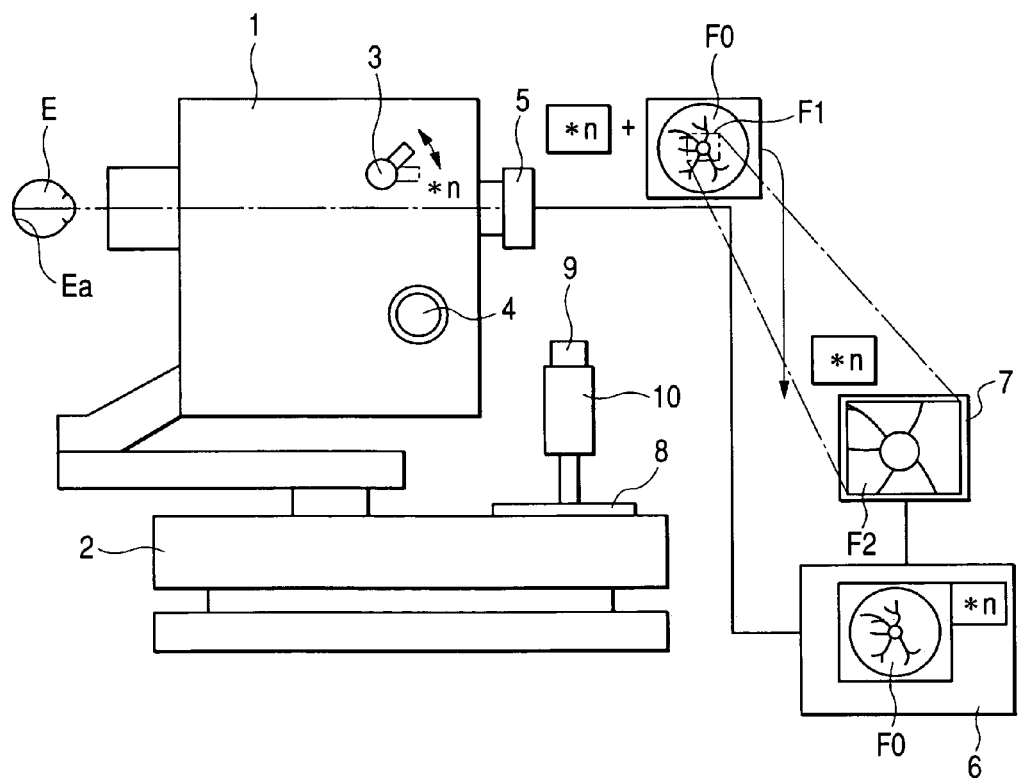
FIG. 5 is an explanatory view showing image taking involving magnification changing.

The term "n-times" described here indicates power relative to *n0 which is the above-mentioned image taking optical system basic imaging power. As shown in FIG. 5, an image F1 of a region corresponding to the magnifying power *n is extracted from a *n0 image F0 of the eye fundus portion Ea which is acquired in the moving image mode by the processing unit 32 of the image handling means 6. The center of the image F1 corresponds to the center of the image F0. The extracted *n magnified image F2 is displayed on the display means 7 (step S205).

The extraction of the region corresponding to the magnifying power of n-times may be performed by any of various known image process methods. An example thereof is as follows. When the number of effective image taking pixels of the image taking element 25 in column and row are given by L and W, respectively, the number of pixels in the region extracted at n-times power in column and row are calculated from Ln=INT(L/n) and Wn=INT(W/n), respectively. Here, "INT( )" indicates a function for rounding a real number in ( ) to obtain an integral number.

Pixel addresses Cx and Cy corresponding to positions of pixels near an imaging center of the image in the image taking element 25 are determined. Pixel data in an area defined by Ln and Wn around the pixel addresses are extracted from the *n0 image F0 and reconstructed to obtain an image. Therefore, the *n magnified image F2 can be extracted from the *n0 image F0.

When the image taking switch 9 is pressed to perform the still image taking in a state in which the magnification changing switch 3 is set to the magnifying power *n (step S206), the moving image examination is stopped by the control means 27 (step S207). The processing unit 32 in the image handling means 6 causes the recording means 33 to record the *n0 image F0 with the magnifying power *n appended thereto as header information (step S209) without producing the *n magnified image F2 from the *n0 image F0 taken by the electronic image taking means 5 (step S208).

In this case, the information of *n and the image data may be separately stored without appending the information of *n to the image data and associated with each other to construct a database.

Figure 6:
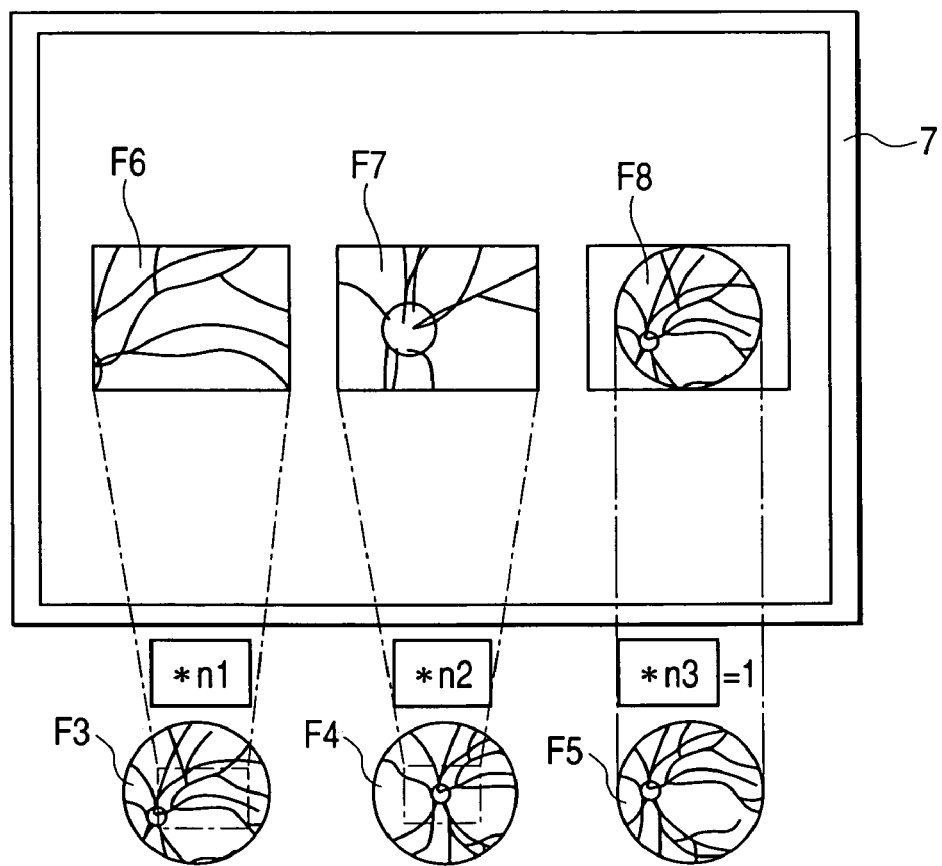
FIG. 6 is an explanatory view showing a display example of a taken image after magnification changing.

FIG. 6 shows an example in which images F3, F4, and F5 which are taken as described above and recorded in the image handling means 6 are selected with a selection switch provided on the operating panel 8, a touch sensor provided on the display means 7, or the like according to a known selection method using an image list, a thumbnail, or the like, and the selected images are displayed on the display means 7.

In the image handling means 6, information on the magnifying power is appended to each of the images F3, F4, and F5 and recorded. That is, the image F3 is appended with information of *n1, the image F4 with *n2, and the image F5 with *n3 (unit magnifying power). These images are recorded as *n0 images in the recording means 33.

Figure 7:
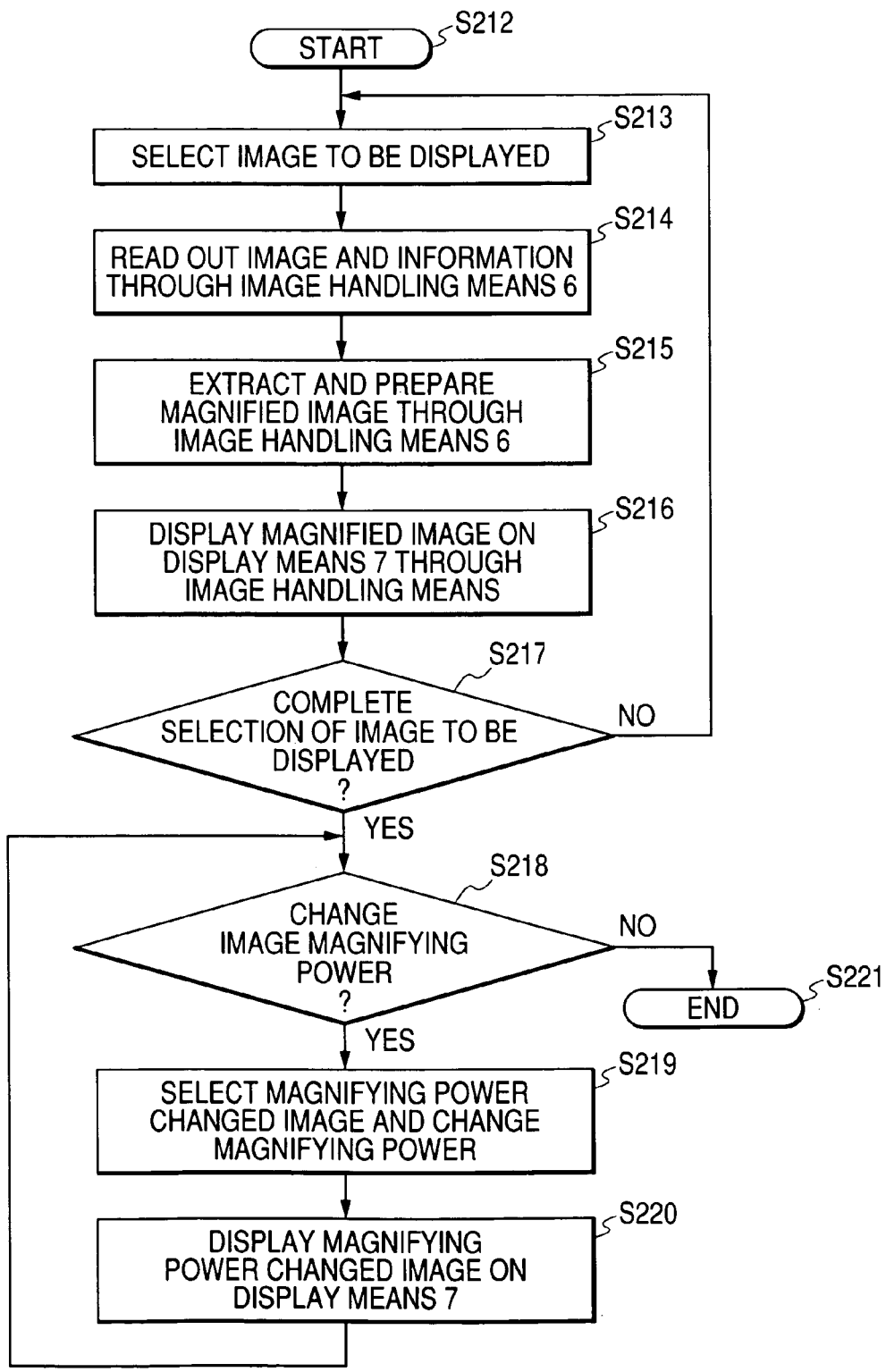
FIG. 7 a flow chart showing a display operation of the taken image after magnification changing.

For example, according to a flow chart shown in FIG. 7, when an image selection signal for the image F3 is input from the control means 27 to the image handling means 6 (step S213), the processing unit 32 reads out the image F3 and *n1 from the recording means 33 (step S214). Then, as described with respect to FIG. 5, the processing unit 32 extracts a region corresponding to *n1 from the *n0 image F3 to prepare an image F6 and causes the display means 7 to display the magnified image (steps S215 and S216). The same process is successively performed on the images F4 and F5. As shown in FIG. 6, a *n2 image F7 of the image F4 and a *n3 image F8 of the image F5 are displayed in parallel.

As described above, when images are displayed in a reproduction mode desired for image taking, the images are represented based on the field of view with which the images were initially examined at image taking. When a signal for changing image display power is input to the control means 27 with a magnifying power changing switch provided in the operating panel 8 (steps S218 and S219), the control means 27 transmits an instruction to the image handling means 6 so as to perform a corresponding image process. In response to the instruction, the processing unit 32 of the image handling means 6 can change the display power of the selected image and perform an image display process on the display means 7 (step S220). When the display power is changed, it is possible to view a peripheral region of the initially displayed image and conduct a detail examination at a higher power.

Figure 8:
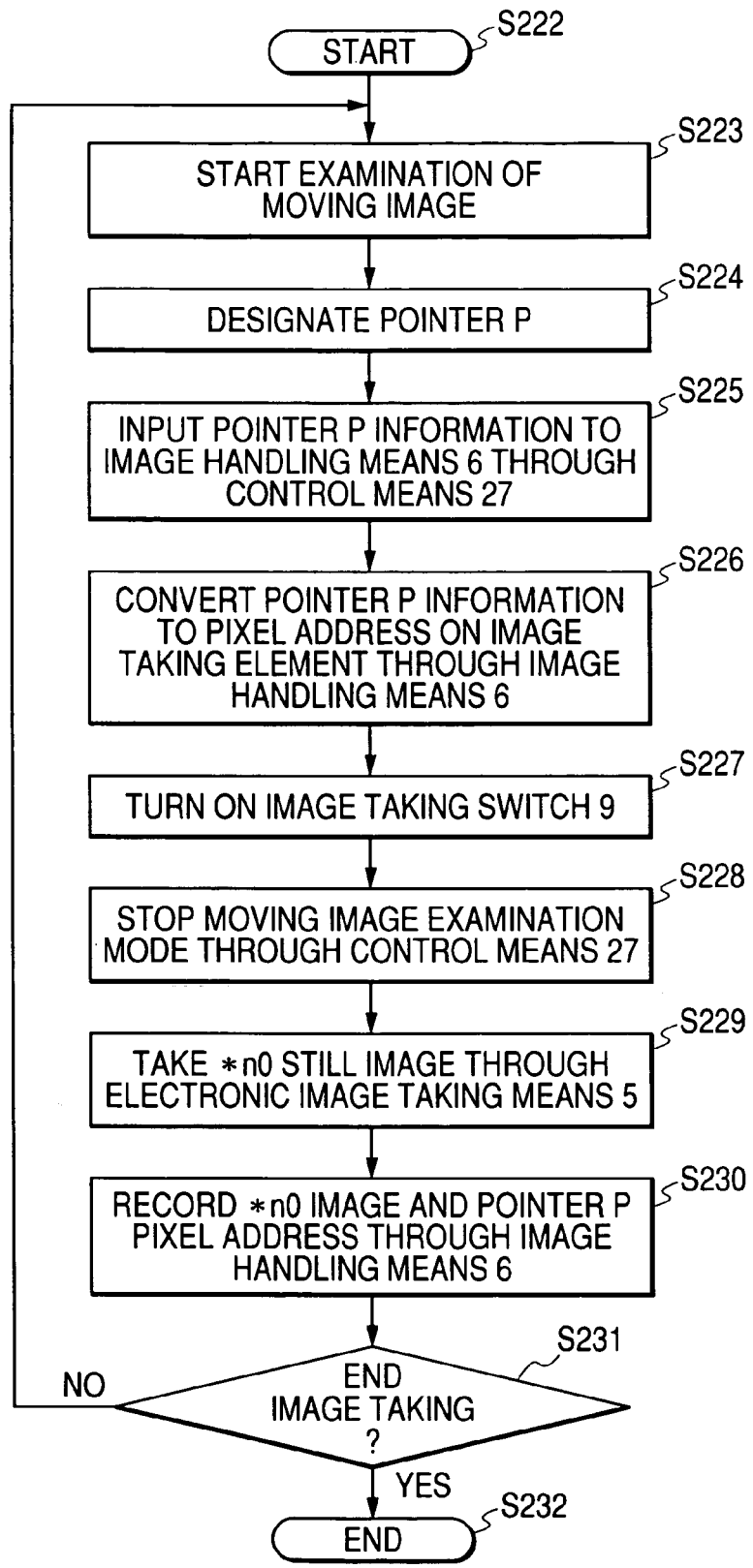
FIG. 8 is a flow chart showing an image taking operation involving eye-point inputting.
Figure 9:
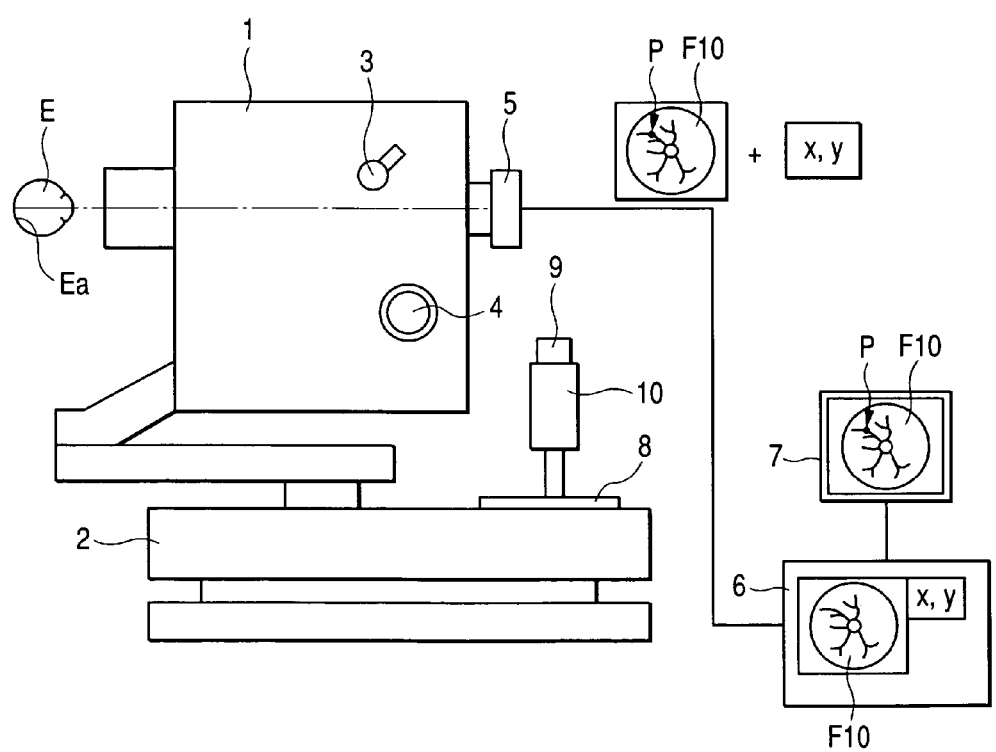
FIG. 9 is an explanatory view showing image taking involving eye-point inputting.

FIG. 8 is a flow chart showing an image taking operation according to a second embodiment of the present invention. As shown in FIG. 9, an examiner conducts an alignment with the eye to be examined E while viewing a moving image F10 displayed on the display means 7 (step S223). During this process, a pointer is moved on the moving image F10 through the control means 27 by the operation of a pointer switch provided in the operating panel 8 to designate a pointer P (step S224). The information of the pointer P is sent to the image handling means 6 (step S255). In the image handling means 6, the processing unit 32 converts the position of the designated pointer P to a pixel address P=(x, y) on the image taking element 25 (step S226). When the image taking switch 9 is pressed for image taking (step S227), in the image handling means 6, the pixel address P is appended to the taken image F10, which is then stored in the recording means 33 (steps S228 to S230).

Figure 10:
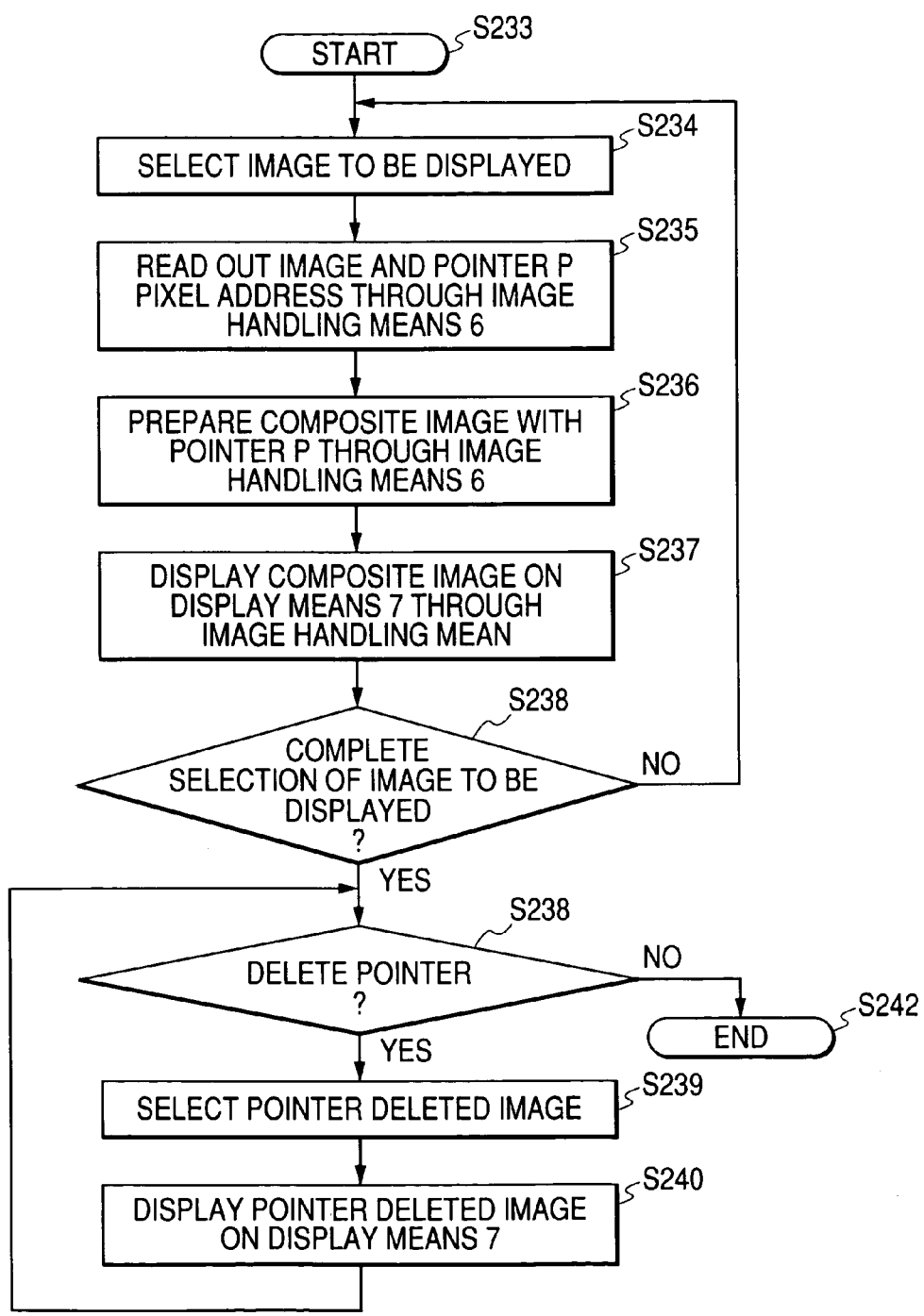
FIG. 10 is a flow chart showing a display operation for image taking involving eye-point inputting.
Figure 11:
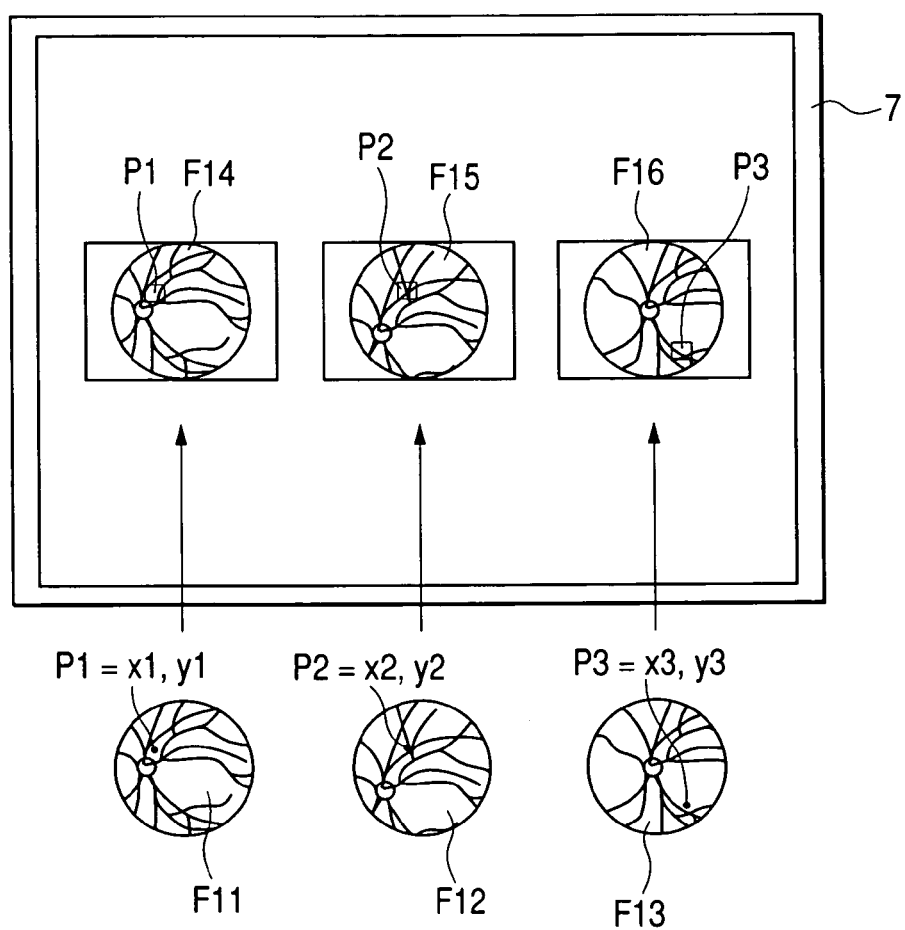
FIG. 11 is an explanatory view showing a display example in image taking involving eye-point inputting.

FIG. 10 is a flow chart illustrating how a composite image of the image taken as described above is displayed. FIG. 11 shows an example in which images F11, F12, and F13 recorded in the image handling means 6 after the above-mentioned image taking are displayed on the display means 7 in the reproduction mode described above.

The images F11, F12, and F13 which are taken as described above and recorded in the image handling means 6 are selected (step S234). In the image handling means 6, the processing unit 32 reads out the recorded image F1 and a pixel address (P1) of a designated point P1 which is appended and recorded during the image taking (step S235). The processing unit 32 prepares a composite image F14 in which a predetermined pointer P1 corresponding to a square area around the pixel address (P1)=(x1, y1) as shown in FIG. 11 is composited on the image F1 (step S236) and causes the display means 7 to display the composite image F14 (S237). The same display process is performed on the images F12 and the F13, so that an image to be displayed F15 and an image to be displayed F16 are displayed as indicated by a pointer P2 and a pointer P3, respectively. Because the pointers P1, P2, and P3 are only for composite display, the pointers can be deleted if necessary (steps S239 to S241).

To set the pointer, the eye-point position of a person who conducts image taking on the examined image may be detected using a known sight line detecting apparatus and input as the position of the pointer. Alternatively, a touch sensor may be provided on the surface of the display means 7, and the position of the pointer may be input by directly touching the examined image displayed on the display means 7.

Figure 12:
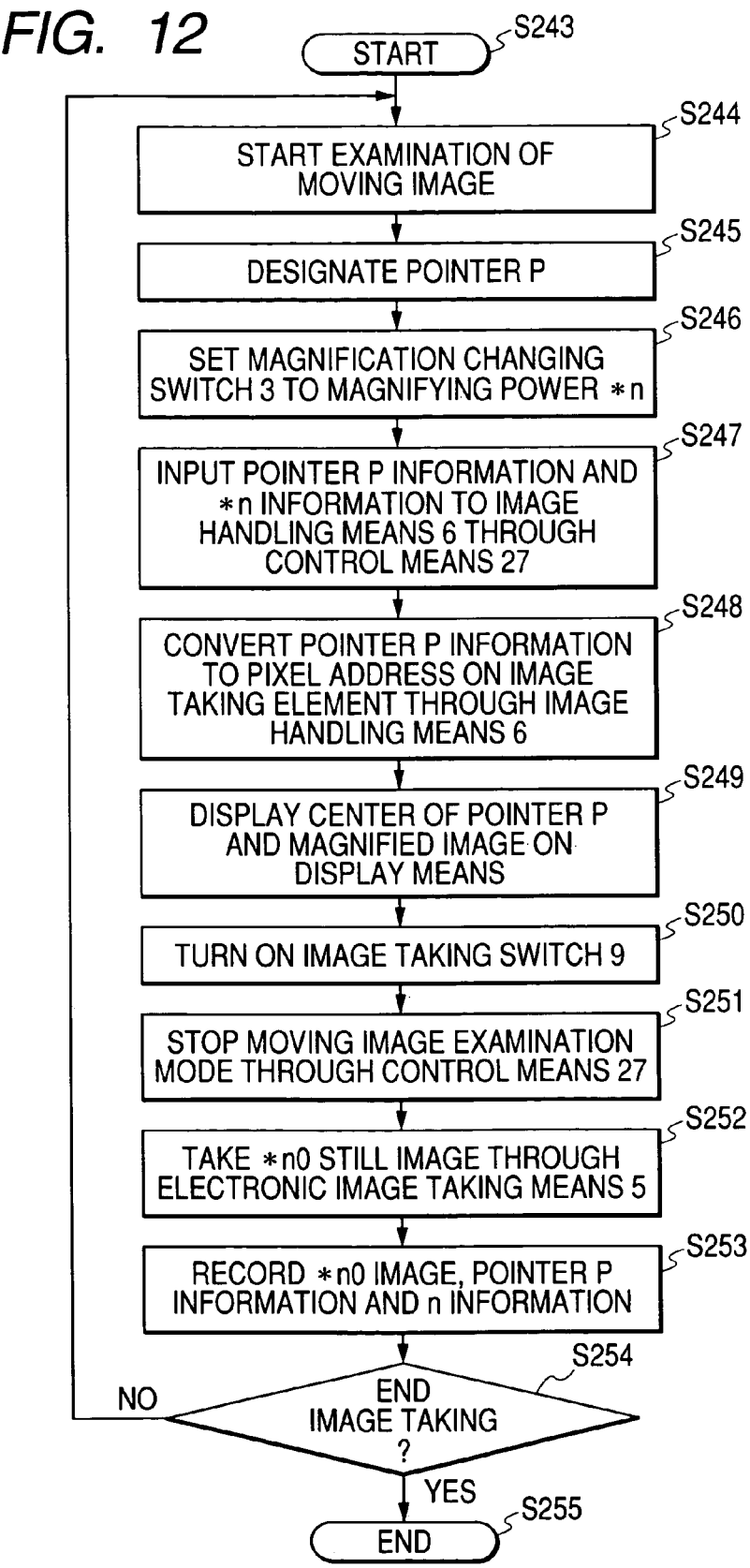
FIG. 12 is a flow chart showing a composite image taking operation involving designated point inputting and magnification changing.
Figure 13:
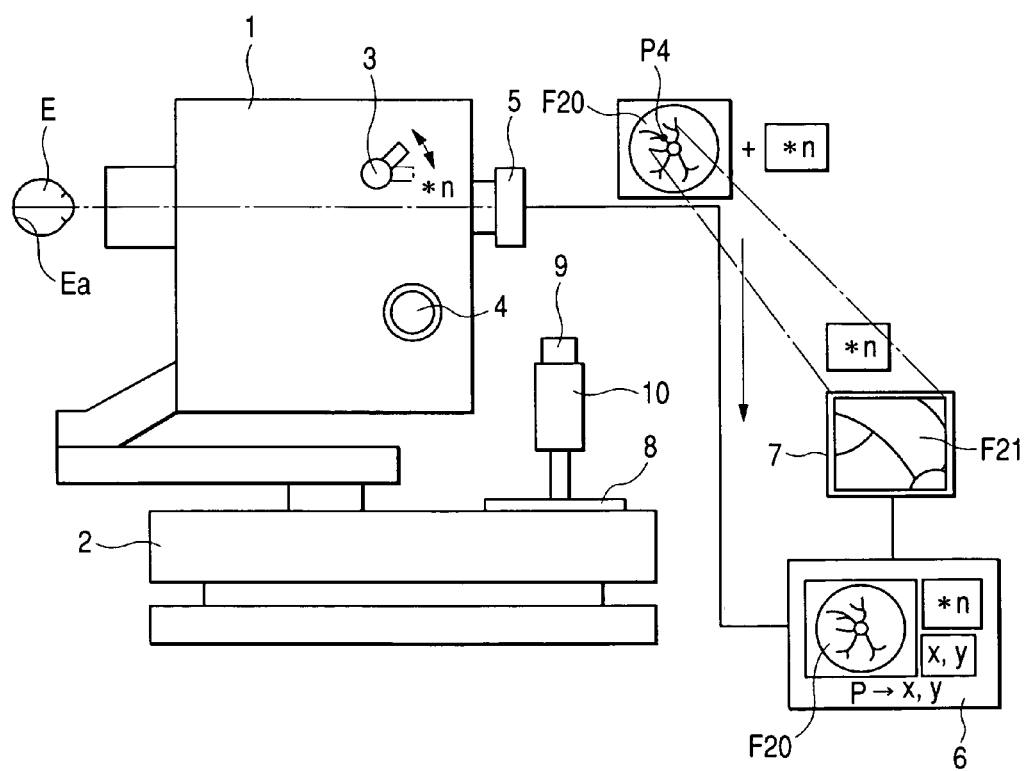
FIG. 13 is an explanatory view showing the composite image taking involving the designated point inputting and the magnification changing.

FIG. 12 is a flow chart for image taking according to a third embodiment of the present invention. In FIG. 13, as described above, a moving image examination is conducted on an eye fundus image F20 of the eye fundus Ea of the eye to be examined E, which is taken by the electronic image taking means 5. During the examination, a pointer P4 is designated as described above and the magnification changing switch 3 is operated to set the magnifying power to n-times (*n) (steps S244 to S246). Then, the processes described in FIGS. 4 and 8 are performed in a composite manner, so that a *n magnified image F21 with the pointer P4 as the center thereof is displayed on the display means 7 (steps S247 to S249). When the image taking switch 9 is pressed to perform the still image taking (steps S250 to S252), the processes described in FIGS. 4 and 8 are performed in a composite manner. In the image handling means 6, information on the magnifying power *n and the pixel address (P)=(x, y) is appended to the *n0 image F20 as header information, and recorded (S253).

In order to facilitate the alignment with the eye to be examined E, the *n0 image may be displayed without displaying the magnified image F21 during the examination. A switching means for switching between the *n0 image and the magnified image F21 may be provided.

Figure 14:
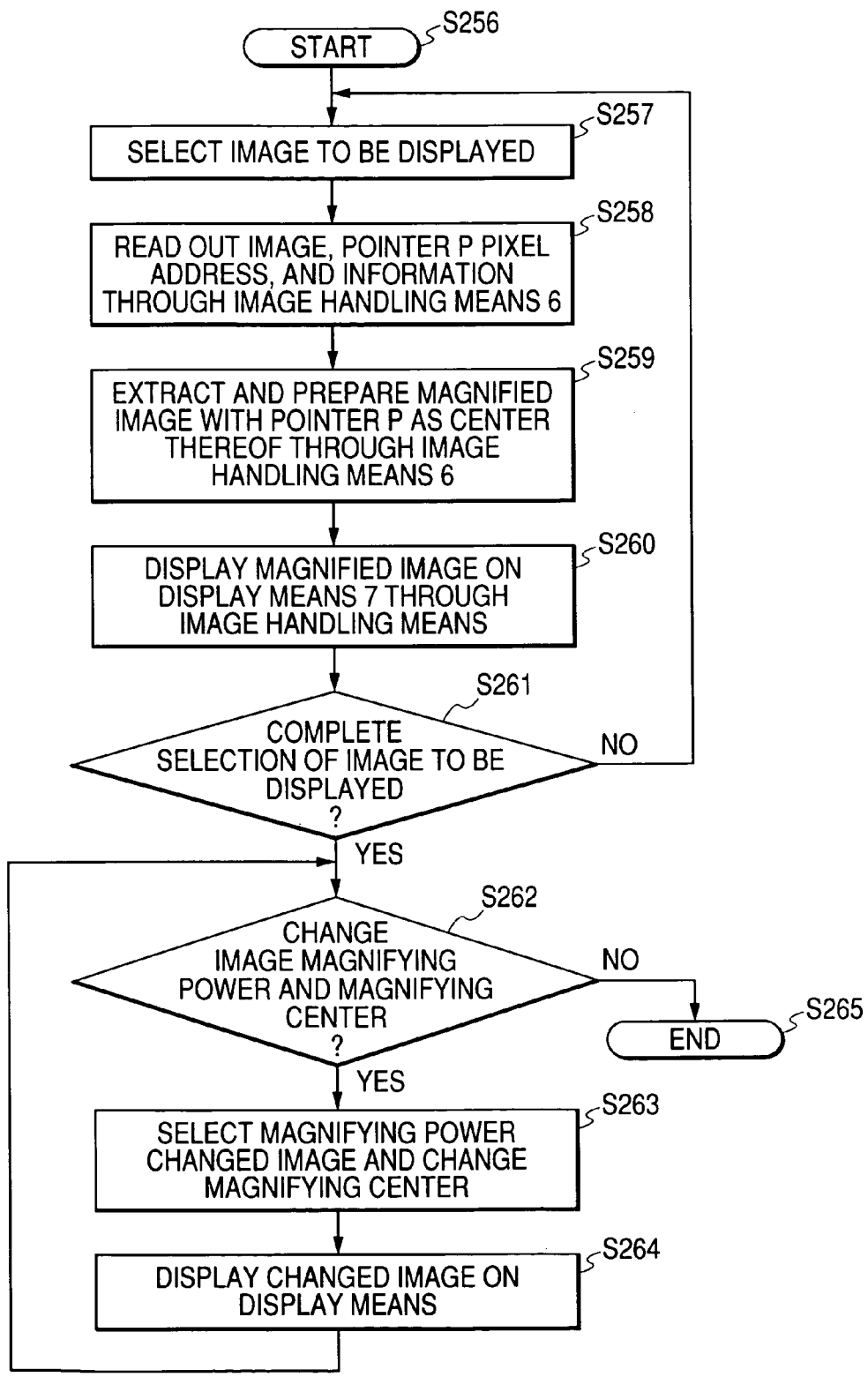
FIG. 14 is a flow chart showing an operation for displaying a composite image taken through image taking involving the designated point inputting and the magnification changing.
Figure 15:
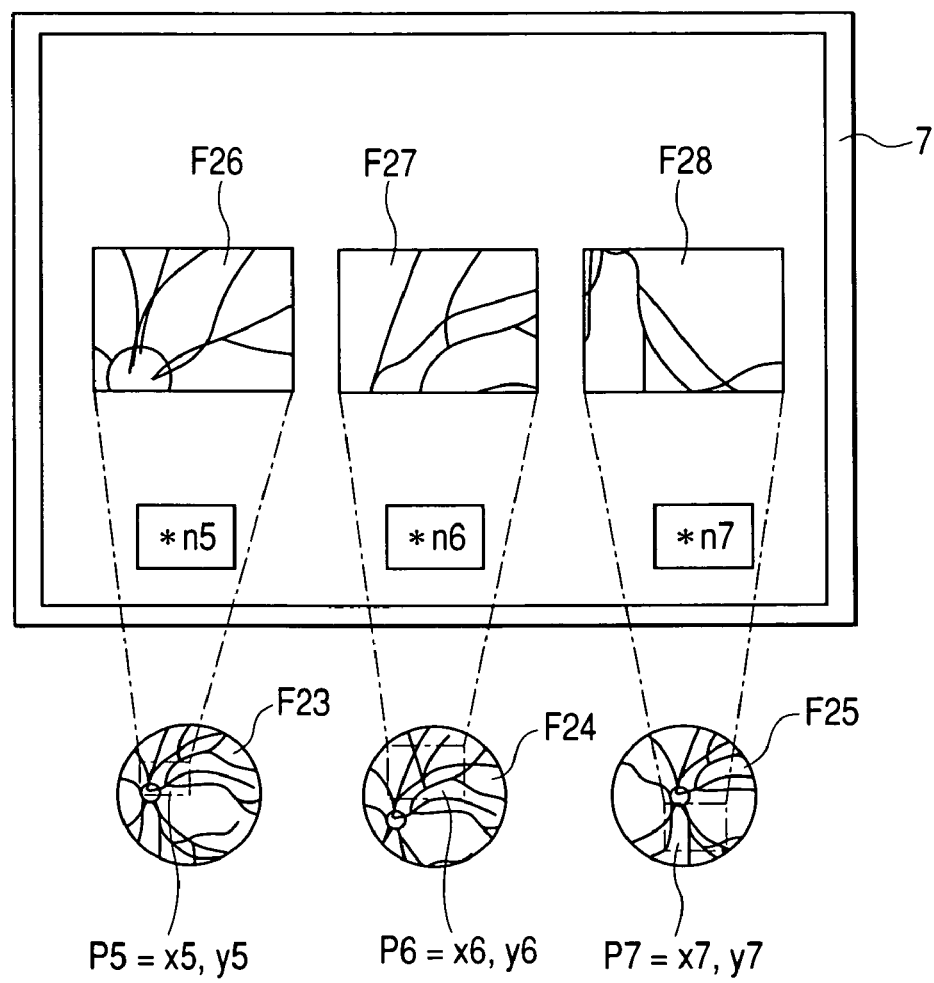
FIG. 15 is an explanatory view showing a display example of the composite image taken through image taking involving the designated point inputting and the magnification changing.

FIG. 14 is a flow chart showing an operation for displaying the taken image. FIG. 15 shows an example in which the recorded still image data is displayed again on the display means 7. As described above, images F23, F24, and F25 are selected (step S257). For example, when the image F23 is to be displayed, the image F23, and a pixel address (P5)=(x5, y5) corresponding to a designated point P5 and magnifying power *n5, which are appended and recorded during the image taking are read out in the image handling means 6 (step S258). The pixel address is converted to a position on the image F23 that is to be displayed. A *n5 magnified image F26 with the pixel address (P5)=(x5, y5) as the center thereof is prepared (step S259) and displayed on the display means 7 (step S260).

The same display process is performed on the images F24 and the F25, so that a *n6 magnified image F27 with a pixel address P6 as the center thereof and *n7 magnified image F28 with a pixel address P7 as the center thereof are displayed. Changing of the magnifying power and the center of the magnified image (steps S262 to S264) are possible by a known means if necessary. Therefore, the description thereof is omitted here.

Figure 16:
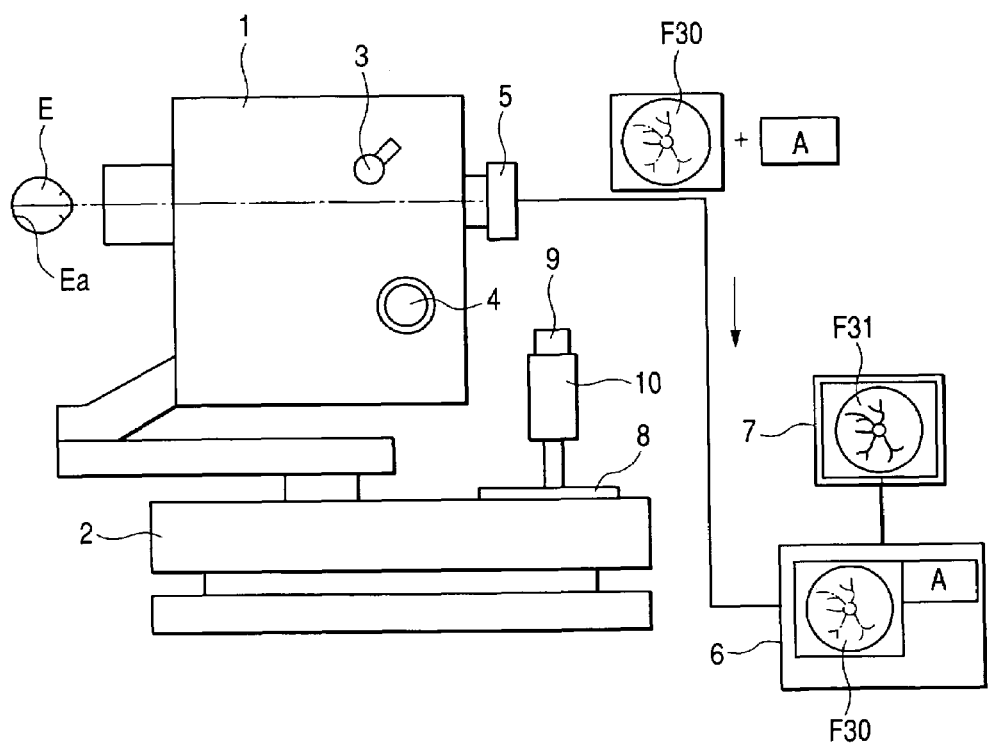
FIG. 16 is an explanatory view showing an edge enhancing image taking.

FIG. 16 shows an apparatus according to a fourth embodiment of the present invention. According to this example, in order to improve the viewability of an examination image during image taking for examination, the examination image is taken while being subjected to an edge enhancing process using a known method.

Figure 17:
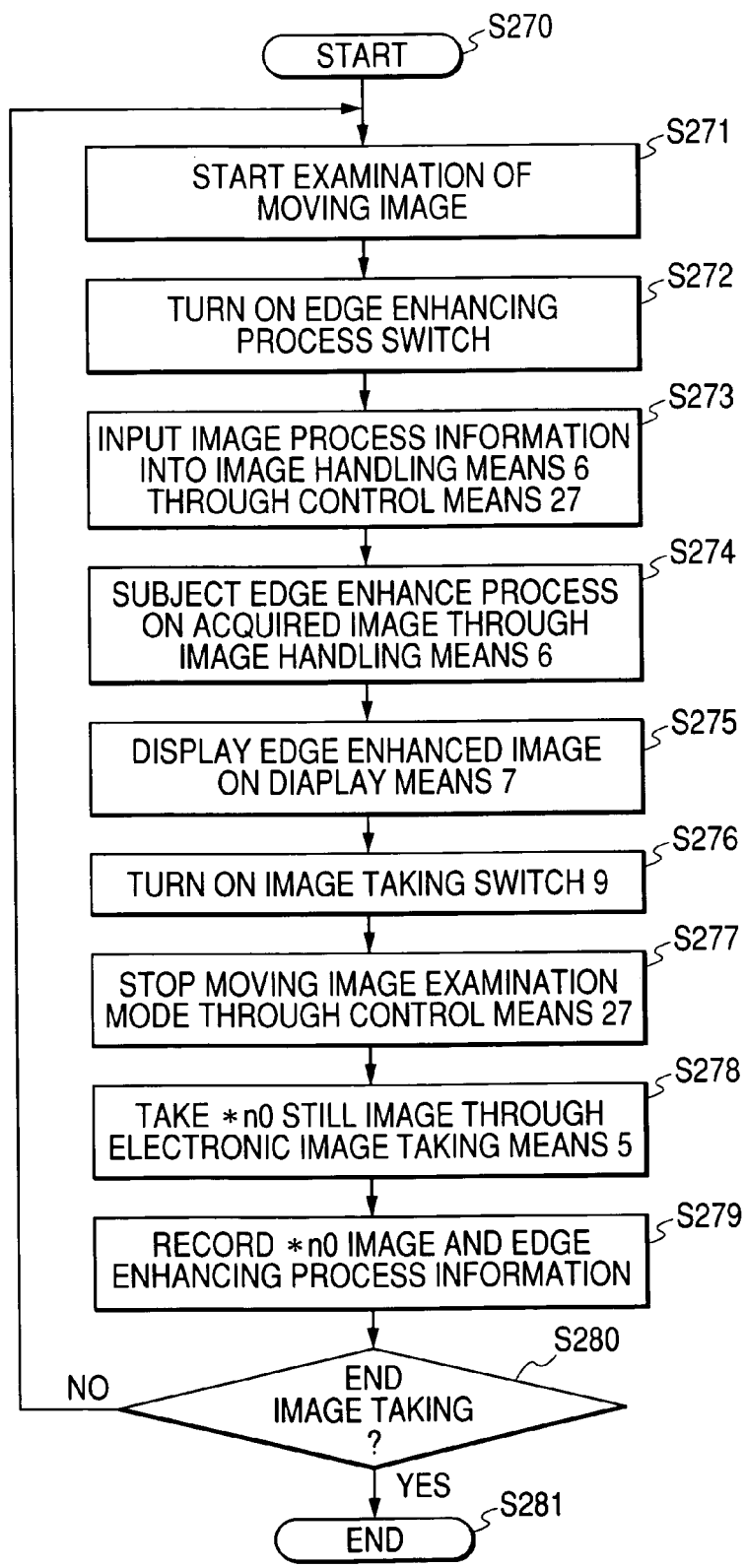
FIG. 17 is a flow chart showing an edge enhancing image taking operation.

FIG. 17 is a flow chart according to the fourth embodiment. An edge enhancing process switch provided in the operating panel 8 is operated during the examination of a moving image F30. In the image handling means 6, a moving image F31 having been subjected to a predetermined edge enhancing process is displayed on the display means 7 (steps S271 to S275). When the image taking switch 9 is pressed to perform the still image taking (steps S276 to S278), the *n0 image F30 is added with edge enhancing process information "A" indicating a manner of the edge enhancing process and recorded in the image handling means 6 (step S279).

Figure 18:
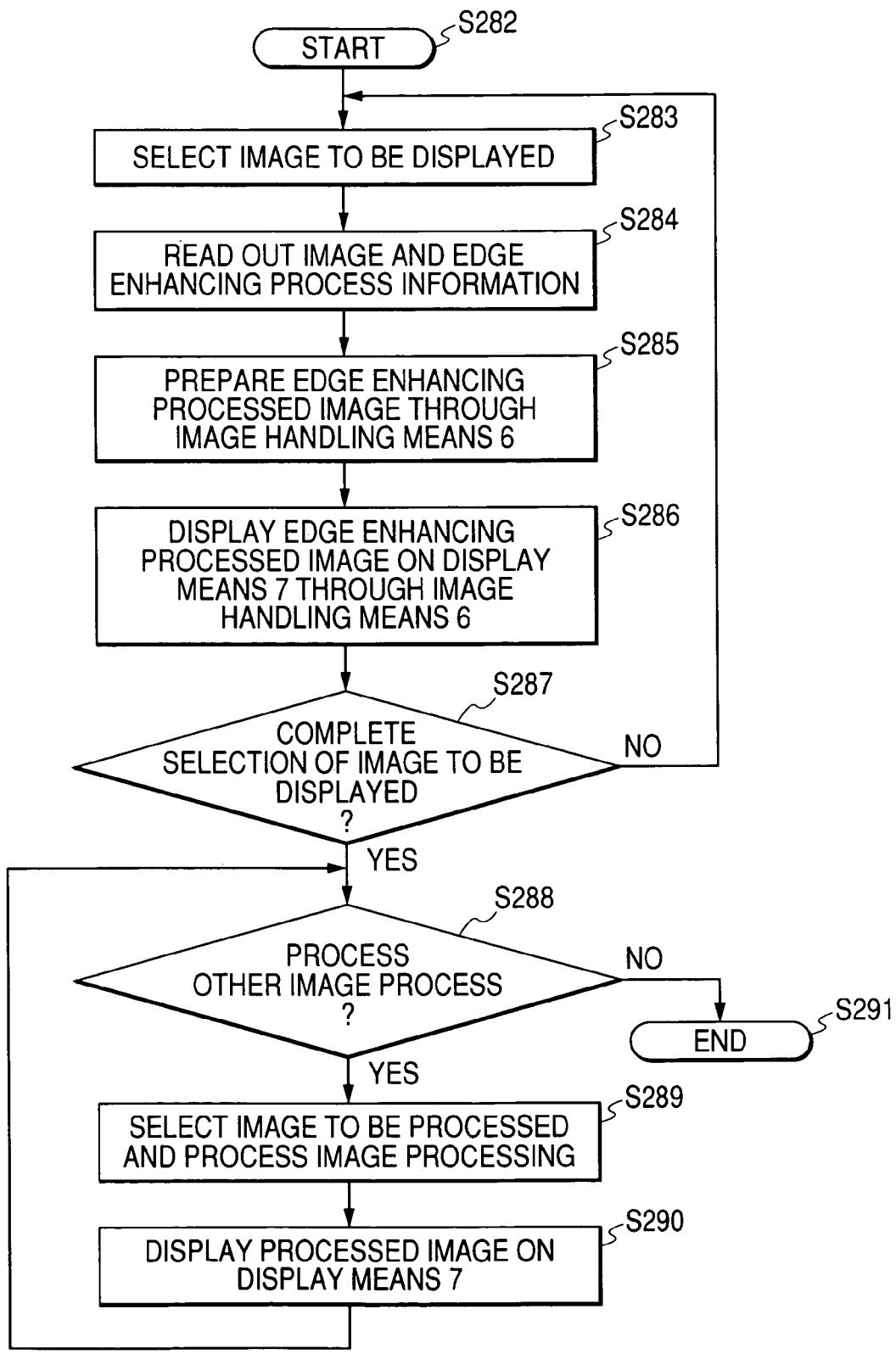
FIG. 18 is a flow chart showing an operation for displaying a taken, edge-enhanced image.

FIG. 18 is a flow chart illustrating how the image taken as described above is displayed. As described above, an image to be displayed is selected (step S283). In the image handling means 6, the image F30 and the edge enhancing process information "A" are read out (step S284). The image F31 obtained by subjecting the image F30 to the edge enhancing process based on the edge enhancing process information "A" is displayed on the display means 7 (steps S285 and S286). If necessary, it can be easily realized using a known method to cancel the edge enhancing process and display the original image F30 (steps S288 to S290).

In addition to the above-mentioned edge enhancing process, a known image process such as a contrast enhancement, an RGB-corrected display, or a band compression and extension can be performed using the same method.

In the present invention, the minimal imaging power (widest view angle) of the image taking optical system with respect to a subject image to be taken is defined as "the image taking optical system basic imaging power." Even in the magnified image taking, a widest view angle image is always taken at this power. The information on the magnifying power with respect to the magnified image is simultaneously recorded together with the taken image. When the taken image is to be displayed again on the display means, the display means always displays not the recorded wide view angle image but a magnified image that has been subjected to the image process based on the magnifying power recorded simultaneously with the taken image. When the display magnifying power is reduced as required, it is possible to view the wide view angle image recorded as an original image. An image of a peripheral portion can be also read at once.

A region of interest for the person who conducts image taking during the examination of the image taking site is simply recorded, and position information of the region of interest is simultaneously recorded together with the taken image. When the taken image is to be displayed again, a maker indicating the region of interest is superposed on the taken image based on the position information of the region of interest which is simultaneously recorded. Therefore, even in the case of a medical image taken such that a site of interest is offset from the center, it is possible to intuitively understand an image taking purpose with respect to the taken medical image.

In order to leave an examination image that has been subjected to an image process, an original image is taken at the image taking optical system basic imaging power by the same method as described above and information related to the image process is simultaneously recorded. When the taken image is to be displayed again, the original image is subjected to the image process based on the information related to the image process and then displayed. Therefore, it is possible to view not only the processed image but also the original image if necessary.

When the thus processed ophthalmologic image is to be read, it is possible to intuitively and speedy understand the image taking purpose, so that the image reading operation can be accurately and efficiently conducted. In addition, an original image in the widest possible range that can be taken can be utilized as needed. Therefore, the efficiency of detailed image reading and the ease of application of the image to multiple purposes are improved, with the result that the use value of a medical image can be significantly increased.

As described above, according to the present invention, it is possible to provide an ophthalmologic image taking apparatus capable of displaying an image in a favorable manner.

This application claims priority from Japanese Patent Application No. 2003-207471 filed on Aug. 13, 2003, which is hereby incorporated by reference herein.

What is claimed is:

1. An ophthalmologic image taking apparatus, comprising:
    an image taking portion for converting an optical image of an eye to be examined, into image data electronically;
    an input portion for inputting a parameter about one of a coordinate, an edge enhancing process, a contrast enhancing process, an RGB correction process, a band compression and extension process based on which a processed image is generated from the image data converted by the image taking portion in a processing portion; and
    a control portion for associating the converted image data with the parameter, and storing the converted image data associated with the parameter in a storing portion,
    wherein the processing portion generates the processed image data from the converted image data stored in the storing portion based on the associated parameter.

2. An ophthalmologic image processing apparatus, comprising:
    a storing portion for storing image data and a parameter about one of a coordinate, an edge enhancing process, a contrast enhancing process, an RGB correction process, a band compression and extension process in association with each other; and
    a processing portion for generating a processed image based on the image data and the parameter to display the generated processed image on a display portion.

3. An ophthalmologic image processing apparatus according to claim 2, wherein the display portion displays a mark based on the coordinate when the coordinate is stored in association with the image data.

* * * * *